(12) United States Patent
Satchivi et al.

(10) Patent No.: US 9,730,446 B2
(45) Date of Patent: Aug. 15, 2017

(54) HERBICIDAL COMPOSITIONS COMPRISING 4-AMINO-3-CHLORO-6-(4-CHLORO-2-FLUORO-3-METHOXY-PHENYL)PYRIDINE-2-CARBOXYLIC ACID OR A DERIVATIVE THEREOF AND PROPYZAMIDE

(71) Applicant: Dow AgroSciences LLC, Indianapolis, IN (US)

(72) Inventors: Norbert M. Satchivi, Carmel, IN (US); Monte R. Weimer, Pittsboro, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/184,414

(22) Filed: Jun. 16, 2016

(65) Prior Publication Data

US 2016/0286804 A1    Oct. 6, 2016

Related U.S. Application Data

(63) Continuation of application No. 14/163,217, filed on Jan. 24, 2014, now abandoned.

(60) Provisional application No. 61/756,903, filed on Jan. 25, 2013.

(51) Int. Cl.
*A01N 43/40* (2006.01)
*A01N 37/18* (2006.01)

(52) U.S. Cl.
CPC .............. *A01N 43/40* (2013.01); *A01N 37/18* (2013.01)

(58) Field of Classification Search
CPC combination set(s) only.
See application file for complete search history.

(56) References Cited

U.S. PATENT DOCUMENTS

| 5,747,422 | A | 5/1998 | Schafer et al. | |
|---|---|---|---|---|
| 8,609,587 | B2 * | 12/2013 | Mann | A01N 37/18 504/100 |
| 8,846,570 | B2 * | 9/2014 | Yerkes | A01N 43/40 504/100 |
| 9,119,397 | B2 * | 9/2015 | Yerkes | A01N 43/40 |
| 2008/0045734 | A1 | 2/2008 | Balko et al. | |
| 2010/0137137 | A1 | 6/2010 | Rosinger et al. | |
| 2011/0287934 | A1 | 11/2011 | Hacker et al. | |
| 2011/0312494 | A1 | 12/2011 | Mann et al. | |
| 2012/0015811 | A1 | 1/2012 | Dave et al. | |
| 2012/0190551 | A1 | 7/2012 | Yerkes et al. | |

FOREIGN PATENT DOCUMENTS

| WO | 9621646 A1 | 7/1996 |
|---|---|---|
| WO | 9632013 A1 | 10/1996 |
| WO | 2009/029518 A2 | 3/2009 |
| WO | 2012/164013 A1 | 12/2012 |

OTHER PUBLICATIONS

Colby, S.R. "Calculating synergistic and antagonistic responses of herbicide combinations," Weeds, vol. 15, 20-22 (1967).
Propyzamide 500 WP label. 4Farmers, PDF dated Aug. 4, 2002, retrieved from the Internet on Apr. 2, 2015 <http://www.herbguide.com.au/Labels/PRPY50_52903-0801.PDF>.
Richer, D.L. "Synergism—a patent view," Pesticide Science, vol. 19(4), 309-315 (1987).
Rummens, F.H.A. "An improved definition of synergistic and antagonistic effects," Weed Science, vol. 23(1), 4-6 (1975).
Webster's New World Dictionary. The World Publishing Company, New York, p. 1127 (1972).
International Search Report and Written Opinion of the International Searching Authority in Application No. PCT/US2014/012913, mailed May 7, 2014, 8 pages.

* cited by examiner

*Primary Examiner* — John Pak
(74) *Attorney, Agent, or Firm* — Michael R. Asam; Meunier Carlin & Curfman, LLC

(57) ABSTRACT

Herbicidal compositions and methods of controlling undesirable vegetation using a combination of (a) a compound of formula (I):

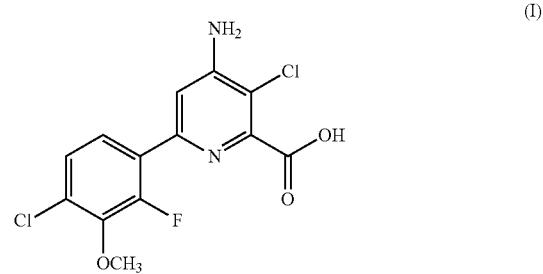

or an agriculturally acceptable salt or ester thereof and (b) propyzamide provide control of undesirable vegetation, e.g., in winter/spring oilseed rape, winter/spring canola, vegetables, *Brassica* spp, ornamentals, rice, wheat, triticale, barley, oats, rye, *sorghum*, corn/maize, sunflower, row crops, pastures, grasslands, rangelands, fallowland, sugarcane, turf, tree and vine orchards, and industrial vegetation management and rights-of-way.

14 Claims, No Drawings

HERBICIDAL COMPOSITIONS COMPRISING 4-AMINO-3-CHLORO-6-(4-CHLORO-2-FLUORO-3-METHOXY-PHENYL)PYRIDINE-2-CARBOXYLIC ACID OR A DERIVATIVE THEREOF AND PROPYZAMIDE

CROSS REFERENCE TO RELATED APPLICATIONS

This application is a continuation of U.S. patent application Ser. No. 14/163,217, filed on Jan. 24, 2014, and claims the benefit of U.S. Provisional Patent Application Ser. No. 61/756,903 filed Jan. 25, 2013, the disclosure of which are expressly incorporated herein by reference.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. However, there remains a need for compositions and methods that are effective in controlling undesirable vegetation.

SUMMARY

Provided herein are herbicidal compositions comprising a herbicidally effective amount of (a) a compound of the formula (I)

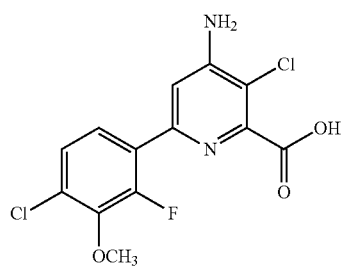

(I)

or an agriculturally acceptable salt or ester thereof, and (b) propyzamide. The compositions may also contain an agriculturally acceptable adjuvant or carrier.

Also provided are methods of controlling undesirable vegetation comprising applying (a) a compound of formula (I) or an agriculturally acceptable ester or salt thereof and (b) propyzamide.

DETAILED DESCRIPTION

Definitions

As used herein, the compound of formula (I) has the following structure:

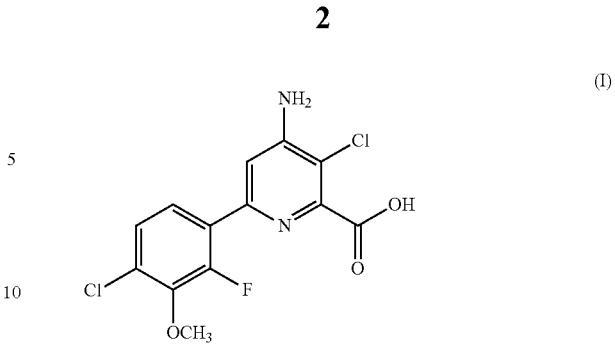

(I)

The compound of formula (I) can be identified by the name 4-amino-3-chloro-6-(4-chloro-2-fluoro-3-methoxyphenyl)-pyridine-2-carboxylic acid and has been described in U.S. Pat. No. 7,314,849 (B2), which is incorporated herein by reference in its entirety. Exemplary uses of the compound of the formula (I) include controlling undesirable vegetation, including e.g., grass, broadleaf and sedge weeds, in multiple non-crop and cropping situations.

As used herein, propyzamide is 3,5-dichloro-N-(1,1-dimethylpropynyl)benzamide. Its herbicidal activity is summarized in Tomlin, C. D. S., Ed. *The Pesticide Manual: A World Compendium*, 15th ed.; BCPC: Alton, 2009 (hereafter "*The Pesticide Manual*, Fifteenth Edition, 2009"). Exemplary uses of propyzamide include its use as a herbicide to selectively control many annual and perennial grasses and some broad-leaved weeds in fruit, vines, lettuce, endive, chicory, brassicas, oilseed rape, legumes, alfalfa, clover, trefoil, sainfoin, artichokes, sugar beet, roses, ornamental trees and shrubs, warm season amenity grass, on fallow land, and in forestry.

As used herein, control of or controlling undesirable vegetation means killing or preventing the vegetation, or causing some other adverse modifying effect to the vegetation e.g., deviations from natural growth or development, regulation, desiccation, retardation, and the like.

As used herein, herbicide and herbicidal active ingredient mean a compound that controls undesirable vegetation when applied in an appropriate amount.

As used herein, a herbicidally effective or vegetation controlling amount is an amount of herbicidal active ingredient the application of which controls the relevant undesirable vegetation.

As used herein, applying or application of a herbicide or herbicidal composition means delivering it directly to the targeted vegetation or to the locus thereof or to the area where control of undesired vegetation is desired. Methods of application include, but are not limited to pre-emergence, post-emergence, foliar, soil, and in-water applications. Described herein are methods of controlling undesirable vegetation through the application of certain herbicide combinations or compositions.

As used herein, plants and vegetation include, but are not limited to, dormant seeds, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can by hydrolyzed, oxidized, metabolized, or otherwise converted, e.g., in plants, water, or soil, to the corresponding carboxylic acid which, depending on the pH, may be in the dissociated or undissociated form.

Exemplary salts include those derived from alkali or alkaline earth metals and those derived from ammonia and amines. Exemplary cations include sodium, potassium, magnesium, triethylammonium (TEA) and cations of the formula:

$$R^1R^2R^3R^4N^+$$

wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methyl-thiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

As used herein in expressing weight ratios, in cases where a salt or ester of the compound of formula (I) is used, the weight referred to for the salt or ester is the acid equivalent weight.

Compositions and Methods

Provided herein are herbicidal compositions comprising a herbicidally effective amount of (a) a compound of the formula (I)

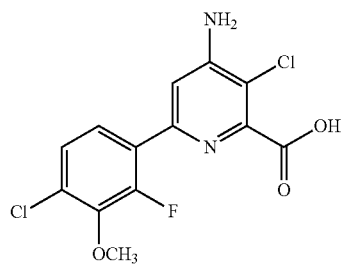

(I)

or an agriculturally acceptable salt or ester thereof, and (b) propyzamide.

Also provided are methods of controlling undesirable vegetation comprising applying a herbicidally effective amount of the compound of formula (I) or an agriculturally acceptable salt or ester thereof and (b) propyzamide. In certain embodiments, the methods employ the compositions described herein.

Furthermore, in some embodiments, the combination of compound (I) or agriculturally acceptable salt or ester thereof and propyzamide exhibits synergism, e.g., the herbicidal active ingredients are more effective in combination than when applied individually. Synergism has been defined as "an interaction of two or more factors such that the effect when combined is greater than the predicted effect based on the response of each factor applied separately." Senseman, S., Ed. Herbicide Handbook. $9^{th}$ ed. Lawrence: Weed Science Society of America, 2007. In certain embodiments, the compositions exhibit synergy as determined by Colby's equation (Colby, S. R. Calculation of the synergistic and antagonistic response of herbicide combinations. *Weeds* 1967, 15, 20-22).

In certain embodiments of the compositions and methods described herein, the compound of formula (I), i.e., the carboxylic acid, is employed. In certain embodiments, a carboxylate salt of the compound of formula (I) is employed, such as the triethylammonium (TEA) or potassium salt. In certain embodiments, a $C_1$-$C_4$ alkyl, e.g., methyl, ester is employed. In certain embodiments, a $C_7$-$C_{10}$ aryl-substituted alkyl, e.g., benzyl, ester is employed.

In some embodiments, the compound of formula (I) or salt or ester thereof and propyzamide are formulated in one composition, tank-mixed, applied simultaneously, or applied sequentially.

Herbicidal activity is exhibited by the compositions when they are applied, i.e. delivered directly to the plant or to the locus of the plant at any stage of growth, or to the area where control is desired. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied as a post-emergence application, pre-emergence application, or in-water application to flooded paddy rice or water bodies (e.g., ponds, lakes and streams), to relatively immature undesirable vegetation to achieve the maximum control of weeds.

In some embodiments, the compositions and methods provided herein are utilized to control weeds in crops, including but not limited to winter/spring oilseed rape, winter/spring canola, vegetables, *Brassica* spp, ornamentals, rice, wheat, triticale, barley, oats, rye, *sorghum*, corn/maize, sunflower, row crops, pastures, grasslands, rangelands, fallowland, sugarcane, turf, tree and vine orchards, industrial vegetation management (IVM) and rights-of-way.

The compositions and methods described herein be used to control undesirable vegetation in glyphosate-tolerant-, glufosinate-tolerant-, dicamba-tolerant-, phenoxy auxin-tolerant-, pyridyloxy auxin-tolerant-, aryloxyphenoxypropionate-tolerant-, acetyl CoA carboxylase (ACCase) inhibitor-tolerant-, imidazolinone-tolerant-, acetolactate synthase (ALS) inhibitor-tolerant-, 4-hydroxyphenyl-pyruvate dioxygenase (HPPD) inhibitor-tolerant-, protoporphyrinogen oxidase (PPO) inhibitor-tolerant-, triazine-tolerant- and bromoxynil-tolerant-crops (such as, but not limited to, soybean, cotton, canola/oilseed rape, sunflower, rice, cereals, corn, turf, tree and vine, sugarcane, etc), for example, in conjunction with glyphosate, glufosinate, dicamba, phenoxy auxins, pyridyloxy auxins, aryloxyphenoxypropionates, ACCase inhibitors, imidazolinones, ALS inhibitors, HPPD inhibitors, PPO inhibitors, triazines, and bromoxynil The compositions and methods may be used in controlling undesirable vegetation in crops possessing multiple or stacked traits conferring tolerance to multiple chemistries and/or inhibitors of multiple modes-of-action. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix.

The compositions and methods provided herein are utilized to control undesirable vegetation. Undesirable vegetation includes, but is not limited to, undesirable vegetation that occurs in oilseed rape, canola, vegetables, *Brassica* spp, ornamentals, rice, wheat, triticale, barley, oats, rye, *sorghum*, corn/maize, sunflower, row crops, pastures, grasslands, rangelands, fallowland, sugarcane, turf, tree and vine orchards, industrial vegetation management (IVM) and rights-of-way.

In certain embodiments, the methods and compositions utilizing the compound of formula (I) or salt or ester thereof in combination with propyzamide are used to provide synergistic control of GLXMA, IPOHE, ABUTH, POLCO, SETFA, BRSNW, AMARE, EPHHL, CHEAL, STEME, VIOTR, CIRRAR, GERSS, POAAN, or VERSS.

In some embodiments, the methods provided herein are utilized to control undesirable vegetation in oilseed rape, canola, drilled crops and cereal crops. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Lolium rigidum* (rigid ryegrass, LOLRI), *Lolium multiflorum* subsp. *Gaudini* (annual ryegrass, LOLMG), *Phalaris minor* Retz. (littleseed canarygrass, PHAMI), *Poa annua* L. (annual bluegrass, POAAN), *Setaria pumila* (Poir.) Roemer & J. A. Schultes (yellow foxtail, SETLU), *Setaria viridis* (L.) Beauv. (green foxtail, SETVI), *Cirsium arvense* (L.) Scop. (Canada thistle, CIRAR), *Galium aparine* L. (catchweed bedstraw, GALAP), *Kochia scoparia* (L.) Schrad. (*kochia*, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in rice. In certain embodiments, the undesirable vegetation is *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Panicum dichotomiflorum* (L.) Michx. (Fall *panicum*, PANDI), *Paspalum dilatatum* Poir. (dallisgrass, PASDI), *Cyperus difformis* L. (smallflower flatsedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus juncoides* Roxb. (Japanese bulrush, SPCJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea hederacea* (L.) Jacq. (ivyleaf morningglory, IPOHE), *Lindernia dubia* (L.) Pennell (low false pimpernel, LIDDU), *Monochoria korsakowii* Regel & Maack (*monochoria*, MOOKA), *Monochoria vaginalis* (Burm. F.) C. Presl ex Kuhth, (*monochoria*, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (mild smartweed, POLHP), *Rotala indica* (Willd.) Koehne (Indian toothcup, ROTIN), *Sagittaria* species, (arrowhead, SAGSS), *Sesbania exaltata* (Raf) Cory/Rydb. Ex Hill (hemp *sesbania*, SEBEX), or *Sphenoclea zeylanica* Gaertn. (gooseweed, SPDZE).

In some embodiments, the methods provided herein are utilized to control undesirable vegetation in range and pasture. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly *sida*, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in row crops and vegetable crops. In certain embodiments, the undesirable vegetation is *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (Fall *panicum*, PANDI), *Panicum miliaceum* L. (wild-proso millet, PANMI), *Setaria faberi* Herrm. (giant foxtail, SETFA),

*Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (Western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Sida spinosa* L. (prickly sida, SIDSP), *Sinapis arvensis* L. (wild mustard, SINAR), *Solanum ptychanthum* Dunal (eastern black nightshade, SOLPT), or *Xanthium strumarium* L. (common cocklebur, XANST).

In some embodiments, the compositions and methods provided herein are utilized to control undesirable vegetation consisting of grass, broadleaf and sedge weeds.

In some embodiments, the combination of compound (I) or agriculturally acceptable ester or salt thereof and propyzamide is used to control *Amaranthus retroflexus* (redroot pigweed, AMARE), *Chenopodium album* (common lambsquarters, CHEAL), *Centaurea cyanus* (cornflower, CENCY), *Descurainia sophia* (flixweed, DESSO), *Conzya canadensis* (horseweed/marestail, ERICA), *Conyza bonariensis* (fleabane, ERIBO), *Erodium cicutarium* (storksbill/redstem filaree, EROCI), *Fumaria officinalis* (common fumitory, FUMOF), *Galeopsis tetrahit* (common hempnettle, GAETE), *Galium aparine* (bedstraw, catchweed/cleavers, GALAP), *Geranium dissectum* (cutleaf *geranium*, GERDI), *Geranium pusillum* (smallflower *geranium*, GERPU), *Glycine max* (volunteer soybean, GLXMA), *Lamium amplexicaule* (henbit, LAMAM), *Lamium purpuruem* (purple deadnettle, LAMPU), *Papaver rhoeas* (common poppy, PAPRH), *Stellaria media* (common chickweed, STEME), *Veronica persica* (Persian speedwell, VERPE), *Linum usitatissimum* (volunteer flax, LIUUT), *Geranium carolinianum* (Carolina *geranium*, GERCA), or *Vicia villosa* (hairy vetch, VICVI).

With regard to the compositions, in some embodiments, the weight ratio of the compound of formula (I) or salt or ester thereof to propyzamide or salt thereof is within the range of from about 1:2240 to about 1:10. In certain embodiments, the weight ratio of the compound of formula (I) or salt or ester thereof to propyzamide or salt thereof is within the range of from about 1:600 to about 1:25. In certain embodiments, the weight ratio of the compound of formula (I) or salt or ester thereof to propyzamide or salt thereof is within the range of from about 1:600 to about 1:30. In certain embodiments, the compositions comprise the compound of formula (I) or its methyl ester, TEA salt, or potassium salt and propyzamide.

With respect to the methods, in certain embodiments, the methods comprise contacting the undesirable vegetation or locus thereof or applying to the soil to prevent the emergence or growth of vegetation a composition described herein. In some embodiments, the composition is applied at an application rate of from about 101 grams active ingredient per hectare (g ai/ha) to about 2250 g ai/ha based on the total amount of active ingredients in the composition. In certain embodiments, the composition is applied at an application rate of from about 250 g ai/ha to about 760 g ai/ha based on the total amount of active ingredients in the composition. In some embodiments, the methods comprise contacting the undesirable vegetation or locus thereof or applying to the soil to prevent the emergence or growth of vegetation with a compound of formula (I) or salt or ester thereof and propyzamide, e.g., sequentially or simultaneously. In some embodiments, the propyzamide is applied at a rate from about 100 g ai/ha to about 2240 g ai/ha and the compound of formula (I) of salt or ester thereof is applied at a rate from about 1 gram acid equivalent per hectare (g ae/ha) to about 10 g ae/ha. In certain embodiments, the methods utilize the compound of formula (I) or its methyl ester, TEA salt, or potassium salt in combination with propyzamide.

The components of the mixtures described herein can be applied either separately or as part of a multipart herbicidal system.

The mixtures described herein can be applied in conjunction with one or more other herbicides to control a wider variety of undesirable vegetation. When used in conjunction with other herbicides, the composition can be formulated with the other herbicide or herbicides, tank-mixed with the other herbicide or herbicides or applied sequentially with the other herbicide or herbicides. Some of the herbicides that can be employed in conjunction with the compositions and methods described herein include, but are not limited to: 4-CPA, 4-CPB, 4-CPP, 2,4-D, 2,4-D choline salt, 2,4-D esters and amines, 2,4-DB, 3,4-DA, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclosulfamuron, cycloxydim, cycluron, cyhalofop-butyl, cyperquat, cyprazine, cyprazole, cypromid, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, fumiclorac, furyloxyfen, glufosinate, glufosinate-ammonium, glufosinate-P-ammonium, glyphosate, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxyfluorfen, paraflufen-ethyl, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyriclor, pyridafol, pyridate, pyriftalid, pyriminobac, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thifensulfuron-methyl, thiobencarb, tiocarbazil, tioclorim, topramezone, tralkoxydim, triafamone, tri-allate, triasulfuron, triaziflam, tribenuron, tribenuron-methyl, tricamba, triclopyr choline salt, triclopyr esters and salts, tridiphane, trietazine, trifloxysulfuron, trifluralin, triflusulfuron, trifop, trifopsime, trihydroxytriazine, trimeturon, tripropindan, tritac tritosulfuron, vemolate, xylachlor and salts, esters, optically active isomers and mixtures thereof.

In some embodiments the methods provided herein are used to control undesirable vegetation in glyphosate-, glufosinate-, dicamba-, phenoxy auxins-, pyridyloxy auxins-, aryloxyphenoxypropionates-, acetyl CoA carboxylase (ACCase) inhibitors-, imidazolinones-, acetolactate synthase (ALS) inhibitors-, 4-hydroxyphenyl-pyruvate dioxygenase (HPPD) inhibitors-, protoporphyrinogen oxidase (PPO) inhibitors-, triazines-inhibitors, or bromoxynil-tolerant crops. Such herbicide tolerant crops may possesses multiple or stacked traits conferring tolerance to multiple herbicides or multiple modes-of-action.

In some embodiments the methods provided herein are used to control undesirable vegetation that is a herbicide resistant or tolerant weed. Such herbicide resistant or tolerant weed may have a biotype with resistance or tolerance to multiple herbicides, multiple chemical classes, or multiple herbicide modes-of-action. For example, the herbicide resistant or tolerant weed may have a biotype resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvyl-shikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action, quinclorac, arylaminopropionic acids, difenzoquat, endothall, or organoarsenicals.

In some embodiments, the compositions described herein are employed in combination with one or more herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, 829148 and N-phenyl-sulfonylbenzoic acid amides, to enhance their selectivity. In some embodiments, the safeners are employed in rice, cereal, corn, or maize settings. In some embodiments, the safener is cloquintocet or an ester or salt thereof. In certain embodiments, cloquintocet is utilized to antagonize harmful effects of the compositions on rice and cereals. In some embodiments, the safener is cloquintocet (mexyl).

In some embodiments, compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank-mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG (400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkyl-naphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

In some embodiments, the concentration of the active ingredients in the compositions described herein is from about 0.0005 to 98 percent by weight. In some embodiments, the concentration is from about 0.0006 to 90 percent by weight. In compositions designed to be employed as concentrates, the active ingredients, in certain embodiments, are present in a concentration from about 0.1 to 98 weight percent, and in certain embodiments about 0.5 to 90 weight percent. Such compositions are, in certain embodiments, diluted with an inert carrier, such as water, before application. The diluted compositions usually applied to weeds or the locus of weeds contain, in certain embodiments, about 0.0005 to 15.0 weight percent active ingredient and in certain embodiments contain about 0.001 to 12.0 weight percent.

The present compositions can be applied to weeds or their locus by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

Examples Evaluation of Postemergent Herbicidal Activity. Seeds or nutlets of the desired test plant species were planted in Sun Gro Metro-Mix® 360 planting mixture, which typically has a pH of 6.0 to 6.8 and an organic matter content of about 30 percent, in plastic pots with a surface area of 64 square centimeters (cm$^2$). When required to ensure good germination and healthy plants, a fungicide treatment and/or other chemical or physical treatment was applied. The plants were grown for 7-21 days (d) in a greenhouse with an approximate 15 hour (h) photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 25 milliliter (mL) glass vial and was dissolved in 4 mL of a 97:3 volume per volume (v/v) mixture of acetone and dimethyl sulfoxide (DMSO) to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Atplus 411F crop oil concentrate, and Triton® X-155 surfactant in a 48.5:39:10:1.5:1.0:0.02 v/v ratio to obtain spray solutions containing the highest application rates. Additional application rates were obtained by serial dilution of 12 mL of the high rate solution into a solution containing 2 mL of a 97:3 v/v mixture of acetone and DMSO and 10 mL of an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain 1/2×, 1/4×, 1/8× and 1/16× rates of the high rate. Compound requirements are based upon a 12 mL application volume at a rate of 187 liters per hectare (L/ha). Formulated compounds were applied to the plant material with an overhead Mandel track sprayer equipped with 8002E nozzles calibrated to deliver 187 L/ha over an application area of 0.503 square meters (m$^2$) at a spray height of 18 inches (43 cm) above the average plant canopy height. Control plants were sprayed in the same manner with the solvent blank.

Treatments consisted of the methyl ester of 4-amino-3-chloro-6-(4-chloro-2-fluoro-3-methoxyphenyl)pyridine-2-carboxylic acid (Cmpd 1) as technical grade material and propyzamide (Kerb 50 W) alone and in combination. The form of compound of formula (I) was applied on an acid equivalent basis and propyzamide was applied on an active ingredient basis.

The treated plants and control plants were placed in a greenhouse as described above and watered by subirrigation to prevent wash-off of the test compounds. After 14 d, the condition of the test plants as compared with that of the untreated plants was determined visually and scored on a scale of 0 to 100 percent where 0 corresponds to no injury and 100 corresponds to complete kill. Some of the compounds tested, application rates employed, plant species tested, and results are given in Table 1.

Results in Table 1 are greenhouse trial results for foliar applied compositions. The observed values in the table refer to percent (%) control rated visually. Colby's equation was used to determine the herbicidal effects expected from the mixtures (Colby, S. R. Calculation of the synergistic and antagonistic response of herbicide combinations. *Weeds* 1967, 15, 20-22). More specifically, the following equation was used to calculate the expected activity of mixtures containing two active ingredients, A and B:

$$\text{Expected} = A + B - (A \times B / 100)$$

A=observed efficacy of active ingredient A at the same concentration as used in the mixture;
B=observed efficacy of active ingredient B at the same concentration as used in the mixture.

The compositions tested, application rates employed, plant species tested, and results are given in Table 1.

The following abbreviations are used in Table 1:
GLXMA *Glycine max* (volunteer soybean)
IPOHE *Ipomoea hederacea* (L.) Jacq. (ivyleaf morningglory)
ABUTH *Abutilon theophrasti* Medik. (velvetleaf)
POLCO *Polygonum convolvulus* L. (wild buckwheat)
SETFA *Setaria faberi* Herrm. (giant foxtail)
BRSNW *Brassica napus* (winter oilseed rape)
AMARE *Amaranthus retroflexus* L. (redroot pigweed)
EPHHL *Euphorbia heterophylla* L. (wild poinsettia)
CHEAL *Chenopodium album* L. (common lambsquarters)
STEME *Stellaria media* (L.) Vill. (common chickweed)
VIOTR *Viola tricolor* L. (wild violet)
CIRAR *Cirsium arvense* (L.) Scop. (Canada thistle)
g ae/ha=grams acid equivalent per hectare
g ai/ha=grams active ingredient per hectare
ob=observed value of % control rated visually
ex=expected value of % control as calculated by Colby's equation
Cmpd I=the methyl ester of the compound of formula (I)

TABLE 1

Synergistic activity of compositions comprising Cmpd I and Propyzamide - percent (%) control rated visually

| Treatment | | GLXMA | | IPOHE | | ABUTH | | POLCO | | SETFA | | BRSNW | | AMARE | |
|---|---|---|---|---|---|---|---|---|---|---|---|---|---|---|---|
| Cmpd I | Propyzamide | | | | | | | | | | | | | | |
| (g ae/ha) | (g ai/ha) | ob | ex | ob | ex | ob | ex | ob | ex | ob | ex | ob | ex | ob | ex |
| 2.5 | 0 | 80 | — | 20 | — | 87 | — | 35 | — | 0 | — | 0 | — | 50 | — |
| 5 | 0 | 87 | — | 38 | — | 85 | — | 25 | — | 5 | — | 0 | — | 58 | — |
| 10 | 0 | 100 | — | 43 | — | 90 | — | 48 | — | 35 | — | 10 | — | 77 | — |
| 0 | 285 | 10 | — | 10 | — | 5 | — | 5 | — | 0 | — | 5 | — | 0 | — |
| 0 | 570 | 15 | — | 17 | — | 0 | — | 15 | — | 0 | — | 20 | — | 10 | — |
| 2.5 | 285 | 83 | 82 | 55 | 28 | 88 | 87 | 38 | 38 | 0 | 0 | 25 | 5 | 82 | 50 |
| 2.5 | 570 | 88 | 83 | 47 | 33 | 93 | 87 | 68 | 45 | 10 | 0 | 10 | 20 | 82 | 55 |
| 5 | 285 | 95 | 88 | 63 | 45 | 94 | 86 | 50 | 29 | 10 | 5 | 15 | 5 | 88 | 58 |

TABLE 1-continued

Synergistic activity of compositions comprising Cmpd I and Propyzamide - percent (%) control rated visually

| 5  | 570 | 97  | 89  | 70 | 49 | 96 | 85 | 63 | 36 | 40 | 5  | 30 | 20 | 86 | 63 |
| 10 | 285 | 96  | 100 | 78 | 49 | 96 | 91 | 80 | 50 | 60 | 35 | 18 | 15 | 91 | 77 |
| 10 | 570 | 100 | 100 | 78 | 53 | 98 | 90 | 80 | 55 | 68 | 35 | 30 | 28 | 92 | 79 |

| Treatment | | EPHHL | | CHEAL | | STEME | | VIOTR | | CIRAR | |
|---|---|---|---|---|---|---|---|---|---|---|---|
| Cmpd I | Propyzamide | | | | | | | | | | |
| (g ae/ha) | (g ai/ha) | ob | ex | ob | ex | ob | ex | ob | ex | ob | ex |
|---|---|---|---|---|---|---|---|---|---|---|---|
| 2.5 | 0   | 85  | —   | 82 | —  | 50 | —  | 30 | —  | 47 | —  |
| 5   | 0   | 93  | —   | 90 | —  | 57 | —  | 43 | —  | 53 | —  |
| 10  | 0   | 100 | —   | 91 | —  | 72 | —  | 62 | —  | 65 | —  |
| 0   | 285 | 0   | —   | 0  | —  | 7  | —  | 0  | —  | 0  | —  |
| 0   | 570 | 0   | —   | 0  | —  | 75 | —  | 0  | —  | 0  | —  |
| 2.5 | 285 | 89  | 85  | 85 | 82 | 73 | 53 | 60 | 30 | 60 | 47 |
| 2.5 | 570 | 94  | 85  | 89 | 82 | 67 | 88 | 65 | 30 | 68 | 47 |
| 5   | 285 | 98  | 93  | 92 | 90 | 85 | 60 | 67 | 43 | 70 | 53 |
| 5   | 570 | 99  | 93  | 92 | 90 | 77 | 89 | 75 | 43 | 72 | 53 |
| 10  | 285 | 100 | 100 | 93 | 91 | 87 | 74 | 78 | 62 | 80 | 65 |
| 10  | 570 | 100 | 100 | 94 | 91 | 92 | 93 | 78 | 62 | 82 | 65 |

Field Trial

Multiple small plot research experiments were conducted to evaluate efficacy and tolerance of winter oilseed rape to compositions described herein. Typical small plots (2-4×4-10 meters (m)) were used in growers' fields under natural conditions with normal commercial cultural practices. Backpack sprayers were used to apply all treatments based on unit area. The methyl ester of formula (I) and propyzamide were tested alone and in combination at varying rates. Application water volume was 150 L/ha. Crop stage was at Growth Stage 39-50. Visual crop injury ratings were collected 32, 49, and 74 days after treatment. In each case the rating was 0% injury. Control of GERSS, POAAN, and VERSS was evaluated visually at 32, 58, and 80 days after application. The observed visual percent (%) control values are reported in the following Tables 2-4. The reported values are means. Means followed by the same letter do not significantly differ (P=0.05, Student-Newman-Keuls).

The following abbreviations are used in Tables 2-4:
GERSS *Geranium* sp. (cranesbill)
POAAN *Poa annua* (annual bluegrass)
VERSS *Veronica* sp. (speedwell)
g ae/ha=grams acid equivalent per hectare
g ai/ha=grams active ingredient per hectare
ob=observed value
ex=expected value as calculated by Colby's equation
Cmpd I=the methyl ester of the compound of formula (I)
DAAA=days after application A

TABLE 2

Synergistic activity of compositions comprising Cmpd I and Propyzamide - percent (%) control rated visually 32 DAAA

| Treatment | | GERSS | | POAAN | | VERSS | |
|---|---|---|---|---|---|---|---|
| Cmpd I | Propyzamide | | | | | | |
| (g ae/ha) | (g ai/ha) | ob | ex | ob | ex | ob | ex |
|---|---|---|---|---|---|---|---|
|      | 250 | 5.0 e    | —    | 12.5 cd  | —    | 43.8 a-d | —    |
|      | 500 | 20.0 de  | —    | 15.0 cd  | —    | 60.0 abc | —    |
|      | 750 | 18.8 de  | —    | 37.5 a-d | —    | 54.3 a-d | —    |
| 1.25 |     | 42.5 cd  | —    | 7.5 cd   | —    | 10.0 cd  | —    |
| 2.5  |     | 42.5 cd  | —    | 10.0 cd  | —    | 26.3 a-d | —    |
| 5    |     | 89.3 ab  | —    | 6.3 cd   | —    | 45.0 a-d | —    |
| 7.5  |     | 91.3 ab  | —    | 28.8 bcd | —    | 81.3 a   | —    |
| 1.25 | 250 | 65.0 abc | 45.4 | 15.0 cd  | 19.1 | 14.6 bcd | 49.4 |
| 1.25 | 500 | 42.5 cd  | 54.0 | 35.0 a-d | 21.4 | 71.3 ab  | 64.0 |
| 1.25 | 750 | 56.3 bc  | 53.3 | 72.5 a   | 42.2 | 87.5 a   | 58.9 |
| 2.5  | 250 | 45.0 cd  | 45.4 | 35.0 a-d | 21.3 | 73.8 ab  | 58.6 |
| 2.5  | 500 | 71.3 abc | 54.0 | 37.5 a-d | 23.5 | 75.0 ab  | 70.5 |
| 2.5  | 750 | 65.0 abc | 53.3 | 48.8 abc | 43.8 | 92.5 a   | 66.3 |
| 5    | 250 | 90.0 ab  | 89.8 | 26.3 bcd | 18.0 | 83.0 a   | 69.1 |
| 5    | 500 | 86.8 ab  | 91.4 | 45.0 a-d | 20.4 | 77.5 ab  | 78.0 |
| 5    | 750 | 86.8 ab  | 91.3 | 46.3 a-d | 41.4 | 91.3 a   | 74.9 |
| 7.5  | 250 | 90.0 ab  | 91.7 | 36.3 a-d | 37.7 | 72.5 ab  | 89.5 |
| 7.5  | 500 | 92.0 ab  | 93.0 | 38.8 a-d | 39.5 | 94.3 a   | 92.5 |
| 7.5  | 750 | 94.5 a   | 92.9 | 61.3 ab  | 55.5 | 91.3 a   | 91.5 |

TABLE 3

Synergistic activity of compositions comprising Cmpd I and Propyzamide - percent (%) control rated visually 58 DAAA

| Treatment | | GERSS | | POAAN | |
|---|---|---|---|---|---|
| Cmpd I (g ae/ha) | Propyzamide (g ai/ha) | ob | ex | ob | ex |
| | 250 | 17.5 d | — | 12.5 e | — |
| | 500 | 35.0 bcd | — | 67.5 bcd | — |
| | 750 | 25.0 cd | — | 92.5 ab | — |
| 1.25 | | 62.5 abc | — | 11.3 e | — |
| 2.5 | | 57.5 abc | — | 15.0 e | — |
| 5 | | 77.5 a | — | 12.5 e | — |
| 7.5 | | 91.3 a | — | 28.8 e | — |
| 1.25 | 250 | 77.0 a | 69.1 | 83.0 abc | 22.4 |
| 1.25 | 500 | 58.8 abc | 75.6 | 82.5 abc | 71.2 |
| 1.25 | 750 | 92.3 a | 71.9 | 99.0 a | 93.3 |
| 2.5 | 250 | 70.0 ab | 64.9 | 60.0 cd | 25.6 |
| 2.5 | 500 | 67.5 ab | 72.4 | 74.5 a-d | 72.4 |
| 2.5 | 750 | 57.5 abc | 68.1 | 88.8 ab | 93.6 |
| 5 | 250 | 82.5 a | 81.4 | 53.8 d | 23.4 |
| 5 | 500 | 78.8 a | 85.4 | 52.5 d | 71.6 |
| 5 | 750 | 86.8 ab | 83.1 | 90.5 ab | 93.4 |
| 7.5 | 250 | 92.8 a | 92.8 | 72.5 a-d | 37.7 |
| 7.5 | 500 | 98.5 a | 94.3 | 88.8 ab | 76.9 |
| 7.5 | 750 | 93.3 a | 93.5 | 88.8 ab | 94.7 |

TABLE 4

Synergistic activity of compositions comprising Cmpd I and Propyzamide - percent (%) control rated visually 80 DAAA

| Treatment | | GERSS | | POAAN | | VERSS | |
|---|---|---|---|---|---|---|---|
| Cmpd I (g ae/ha) | Propyzamide (g ai/ha) | ob | ex | ob | ex | ob | ex |
| | 250 | 22.5 d | — | 45.0 c | — | 100.0 a | — |
| | 500 | 28.8 bcd | — | 95.0 a | — | 100.0 a | — |
| | 750 | 33.8 a-d | — | 98.3 a | — | 100.0 a | — |
| 1.25 | | 53.8 a-d | — | 16.3 d | — | 80.0 a | — |
| 2.5 | | 67.5 a-d | — | 15.0 d | — | 97.5 a | — |
| 5 | | 69.5 a-d | — | 6.3 d | — | 100.0 a | — |
| 7.5 | | 99.8 a | — | 18.8 d | — | 100.0 a | — |
| 1.25 | 250 | 93.0 a | 64.2 | 88.0 ab | 54.0 | 100.0 a | 100.0 |
| 1.25 | 500 | 88.8 ab | 67.1 | 92.5 a | 95.8 | 100.0 a | 100.0 |
| 1.25 | 750 | 98.8 a | 69.4 | 100.0 a | 98.6 | 97.5 a | 100.0 |
| 2.5 | 250 | 59.8 a-d | 74.8 | 73.8 ab | 53.3 | 97.5 a | 100.0 |
| 2.5 | 500 | 53.8 a-d | 76.9 | 78.8 ab | 95.8 | 95.0 a | 100.0 |
| 2.5 | 750 | 25.0 cd | 78.5 | 92.3 a | 98.6 | 100.0 a | 100.0 |
| 5 | 250 | 71.0 a-d | 76.4 | 57.5 bc | 48.5 | 100.0 a | 100.0 |
| 5 | 500 | 55.0 a-d | 78.3 | 57.5 bc | 95.3 | 100.0 a | 100.0 |
| 5 | 750 | 87.5 abc | 79.8 | 98.3 a | 98.4 | 100.0 a | 100.0 |
| 7.5 | 250 | 100.0 a | 99.8 | 83.3 ab | 55.3 | 100.0 a | 100.0 |
| 7.5 | 500 | 100.0 a | 99.9 | 98.0 a | 95.9 | 100.0 a | 100.0 |
| 7.5 | 750 | 97.5 a | 99.9 | 98.8 a | 98.6 | 100.0 a | 100.0 |

What is claimed is:

1. A method of controlling undesirable vegetation which comprises contacting the vegetation or the locus thereof with or applying to the soil or water to control the emergence or growth of vegetation a herbicidally effective amount of (a) a compound of formula (I)

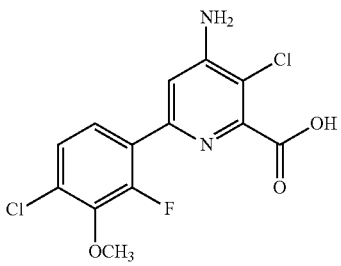

(I)

or an agriculturally acceptable salt or ester thereof and (b) propyzamide, or a salt thereof; wherein the weight ratio of the compound of formula (I) or an agriculturally acceptable salt or ester thereof to propyzamide, or a salt thereof, is from about 1:600 to about 1:50, and wherein the undesirable vegetation is IPOHE, POLCO, SETFA, VIOTR, or CIRAR.

2. The method of claim 1, wherein the propyzamide is applied at a rate from about 100 g ai/ha to about 2240 g ai/ha and the compound of formula (I) or agriculturally acceptable salt or ester thereof is applied at a rate from about 1 g ae/ha to about 10 g ae/ha.

3. The method of claim 1, wherein the propyzamide is applied at a rate from about 250 g ai/ha to about 750 g ai/ha and the compound of formula (I) or agriculturally acceptable salt or ester thereof is applied at a rate from about 1.25 g ae/ha to about 10 g ae/ha.

4. The method of claim 1, wherein the undesirable vegetation is controlled in winter/spring oilseed rape, winter/ spring canola, vegetables, *Brassica* spp, ornamentals, rice, wheat, triticale, barley, oats, rye, *sorghum*, corn/maize, sunflower, row crops, pastures, grasslands, rangelands, fallowland, sugarcane, turf, tree and vine orchards, industrial vegetation management and rights-of-way.

5. The method of claim 1, wherein the undesirable vegetation is immature.

6. The method of claim 1, wherein the (a) and (b) are applied pre-emergently.

7. The method of claim 1, wherein the (a) and (b) are applied post-emergently.

8. The method of claim 1, wherein the undesirable vegetation is controlled in a crop that is tolerant to glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, or bromoxynil.

9. The method of claim 8, wherein the tolerant crop possesses multiple or stacked traits conferring tolerance to multiple herbicides or multiple modes-of-action.

10. The method of claim 8, wherein the undesirable vegetation comprises a herbicide resistant or tolerant weed.

11. The method of claim 10, wherein the resistant or tolerant weed is a biotype with resistance or tolerance to multiple herbicides, multiple chemical classes, or multiple herbicide modes-of-action.

12. The method of claim 11, wherein the resistant or tolerant weed is a biotype resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvylshikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action, quinclorac, arylaminopropionic acids, difenzoquat, endothall, or organoarsenicals.

13. The method of claim 1, wherein (a) is the methyl ester, triethylammonium (TEA) salt, or potassium salt of the compound of formula (I).

14. The method of claim 13, wherein (a) is the methyl ester of the compound of formula (I).

* * * * *